(12) United States Patent
Yang et al.

(10) Patent No.: US 10,591,434 B2
(45) Date of Patent: Mar. 17, 2020

(54) BIO-DETECTION DEVICE AND MANUFACTURING METHOD THEREOF

(71) Applicant: RICHTEK TECHNOLOGY CORPORATION, Zhubei, HsinChu County (TW)

(72) Inventors: Yu-Lin Yang, Xiyu Township (TW); Chun-Hao Chang, Zhubei (TW); Min-Da Wu, Hsinchu County (TW); Hung-Der Su, Hsinchu County (TW); Da-Hong Qian, Boston, MA (US)

(73) Assignee: RICHTEK TECHNOLOGY CORPORATION, Zhubei, Hsinchu ( * ) Notice: Subject to any disclaimer, the term of this patent is extended or adjusted under 35 U.S.C. 154(b) by 388 days.

(21) Appl. No.: 15/495,136

(22) Filed: Apr. 24, 2017

(65) Prior Publication Data

US 2018/0306742 A1 Oct. 25, 2018
US 2019/0227018 A9 Jul. 25, 2019

Related U.S. Application Data

(60) Provisional application No. 62/347,090, filed on Jun. 8, 2016.

(30) Foreign Application Priority Data

Oct. 7, 2016 (TW) .............................. 105132499 A

(51) Int. Cl.
*G01N 27/22* (2006.01)
*B01L 3/00* (2006.01)

(52) U.S. Cl.
CPC .............. *G01N 27/22* (2013.01); *B01L 3/502* (2013.01); *B01L 3/508* (2013.01); *G01N 27/226* (2013.01); *B01L 2200/12* (2013.01); *B01L 2300/0627* (2013.01); *B01L 2300/0645* (2013.01); *B01L 2300/0663* (2013.01); *B01L 2300/0887* (2013.01); *B01L 2300/161* (2013.01)

(58) Field of Classification Search
CPC .. B01L 3/502; B01L 3/508; B01L 2300/0663; B01L 2300/0645; G01N 27/226
See application file for complete search history.

(56) References Cited

U.S. PATENT DOCUMENTS 8,318,099 B2 * 11/2012 Potyrailo ........... G06K 19/0717
250/214.1

* cited by examiner

*Primary Examiner* — Dennis White
(74) *Attorney, Agent, or Firm* — Tung & Associates

(57) ABSTRACT

The invention provides a bio-detection device, including a carrier, a plurality of spacers, an electronic circuit, and a package layer, wherein an open platform is formed. The carrier includes a test region and a signal transmission wiring, wherein the test region is configured to carry a fluid under test. The spacers are located on the test region and electrically connected to two different voltage levels to form a capacitor for sensing a capacitance of the fluid. The spacers are connected to the signal transmission wiring. The electronic circuit receives and processes a sensing signal corresponding to the capacitance of the fluid. The package layer covers a portion of the carrier but does not cover the test region. The open platform is formed whereby a user can easily put in the fluid. The open platform has a bottom which includes the test region, and an area of the open platform is defined by the spacers and the package layer.

7 Claims, 8 Drawing Sheets

BIO-DETECTION DEVICE AND MANUFACTURING METHOD THEREOF

CROSS REFERENCE

The present invention claims priority to U.S. provisional application No. 62/347,090, filed on Jun. 8, 2016, and also claims priority to TW 105132499, filed on Oct. 7, 2016.

BACKGROUND OF THE INVENTION

Field of Invention

The present invention relates to a bio-detection device, which includes an open platform for carrying a fluid under test; the bio-detection device senses a capacitance of the fluid under test to determine a concentration of a component in the fluid.

Description of Related Art

Prior art bio-detection devices typically employ a micro-channel, which is a sealed, thin and long passage, in which the pressure, temperature, surface tension, and/or other factors are controlled whereby a fluid under test moves in the micro-channel to be analyzed. In order to be able to test different fluids, the micro-channel needs to have or to be adjusted to different designs, so the structure and manufacturing process of the micro-channel are very complicated.

Besides, the micro-channel requires a large area for accommodating its main path and shunt paths, and also requires a driving unit for controlling the pressure, temperature, surface tension, or other factors inside the channel, to control the fluid under test in the channel. In short, the micro-channel technique is complicated in structure, manufacturing process and execution process, and it requires a large area.

In view of the demerits of the prior art, the present invention provides a bio-detection device having benefits of easy detection control, compact size, and simple manufacturing process.

SUMMARY OF THE INVENTION

In one perspective, the present invention provides a bio-detection device, which includes: a carrier, including a test region and a signal transmission wiring, the test region being configured to operably carry a fluid under test; a plurality of spacers, located on the test region and electrically connected to at least two different voltage levels to format least one capacitor for sensing a capacitance of the fluid under test, the spacers being coupled to the signal transmission wiring; an electronic circuit, coupled to the signal transmission wiring, and being configured to operably receive and process a sensing signal corresponding to the capacitance of the fluid under test; and a package layer, covering a portion of the carrier but not covering the test region; whereby an open platform is defined for the fluid under test to be put in, the open platform having a bottom which includes the test region, and having an area defined by the spacers and the package layer.

In one embodiment, the bio-detection device further includes a hydrophilic layer which is located on the test region.

In one embodiment, the bio-detection device further includes a rust-proof layer. The rust-proof layer is located on surfaces of the plurality of spacers and located on an exposed surface of the signal transmission wiring.

In one embodiment, the bio-detection device further includes a hydrophilic layer. A portion of the rust-proof layer is located on at least a top and a side of the open platform. The hydrophilic layer is located: (a) on a portion of the open platform where the rust-proof layer does not cover, or (b) on the rust-proof layer and on a portion of the open platform where the rust-proof layer does not cover.

In one embodiment, the spacers are made of a material including: copper, nickel, gold, palladium, copper alloy, nickel alloy, gold alloy, palladium alloy, or a combination thereof; and/or the signal transmission wiring is made of a material including copper, nickel, gold, palladium, copper alloy, nickel alloy, gold alloy, palladium alloy, or a combination thereof. In one embodiment, the rust-proof layer is made of a material including organic solderability preservatives (OSP) to cover the spacers.

In one embodiment, the electronic circuit is located on the carrier and the package layer encapsulates the electronic circuit.

In one embodiment, the package layer is manufactured by a process of open cavity molding, to cover a portion of the carrier outside the outermost spacers on the test region.

In one embodiment, the carrier is manufactured by a process of molded interconnect system.

In one perspective, the present invention provides a manufacturing method of a bio-detection device. The manufacturing method includes: providing a carrier, which includes a test region and a signal transmission wiring; forming a plurality of spacers on the carrier and coupling the spacers to the signal transmission wiring, the spacers being configured to operably sense a capacitance of a fluid under test; and forming a package layer by a process of open cavity molding, to cover a portion of the carrier but not to cover the test region, whereby an open platform is defined to put the fluid under test.

In one embodiment, the manufacturing method further includes: forming an electronic circuit on the carrier and coupling the electronic circuit to the signal transmission wiring, wherein the electronic circuit is configured to operably receive and process a sensing signal generated by the spacers.

In one embodiment, the carrier is manufactured by steps including: providing a substrate; forming the signal transmission wiring on the substrate; encapsulating both the substrate and the signal transmission wiring on the substrate by a filler layer; and removing the substrate, to expose a portion of the signal transmission wiring on a first surface of the filler layer.

In one embodiment, the manufacturing steps of the carrier further include: grinding the filler layer such that another portion of the signal transmission circuit is exposed on a second surface of the filler layer, wherein the second surface is opposite to the first surface.

In one embodiment, the process of open cavity molding for forming the package layer includes: providing a molding plate in contact with the carrier or at least one of the spacers on the carrier; filling a filler flow on the carrier, wherein the spacers form a structure which blocks the filler flow from flowing onto the test region; solidifying the filler flow to form the package layer; and removing the molding plate.

In one embodiment, the molding plate includes an extrusion. When the molding plate is in contact with at least one of the spacers, the extrusion is in contact with an outermost one of the spacers, to block the filler flow from flowing onto the test region.

DESCRIPTION OF THE PREFERRED EMBODIMENTS

The drawings as referred to throughout the description of the present invention are for illustrative purpose only, to show the interrelations between the components, but not drawn according to actual scale.

Figure 1A:
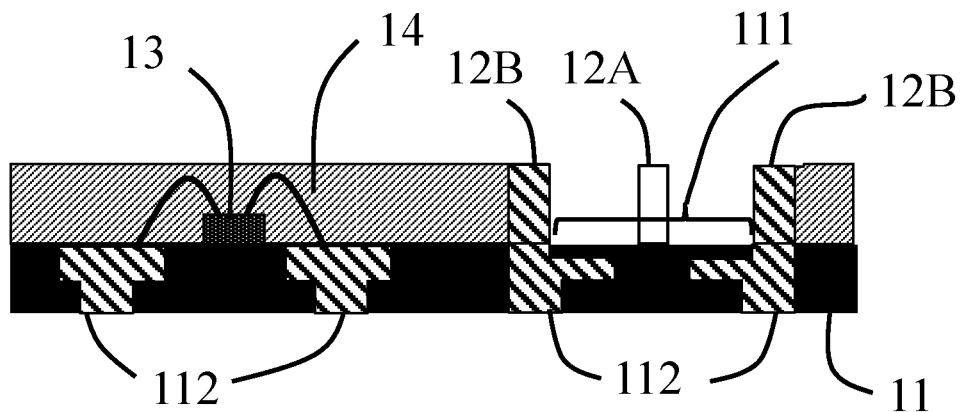
FIGS. 1A, 1B, and 1C show a bio-detection device according to one embodiment of the present invention.
Figure 1B:
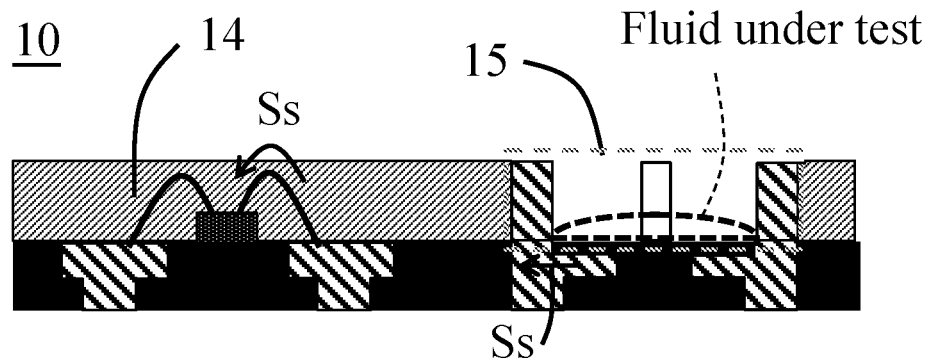
Figure 1C:
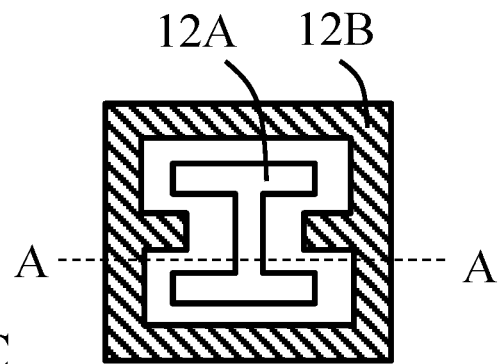

Please refer to cross-section view shown in FIG. 1A, in one perspective, the present invention provides a bio-detection device 10, which includes a carrier 11, a plurality of spacers 12 and 12B (in this embodiment, the spacers for example can be metal spacers), an electronic circuit 13, and a package layer 14. The metal spacers 12A and 12B are electrically connected to two different voltage levels to form a capacitor. The layout of the metal spacers 12A and 12B from top view can be decided according to practical requirements, and the layout is not limited to the layout as shown in figure nor limited to any other specific layout. FIG. 1A is a cross-section view according to the cross-section line A-A in FIG. 1C. If required, the bio-detection device 10 can include more metal spacers electrically connected to the same or different levels of the metal spacers 12A and 12B. The carrier 11 includes a test region 111 and a signal transmission wiring 112 (for simplification of the drawing, the signal transmission wiring 112 is shown schematically, wherein the connection portion of the signal transmission wiring 112 to the metal spacers 12A is not shown in the figure). The spacers 12A and 12B are located on the test region 111 and the test region 111 is configure to operably carry a fluid under test (FIG. 1B). A capacitance of the fluid can be obtained according to the signal taken from the metal spacers 12A and 12B. The fluid for example can be, but is not limited to a mucus, blood, sweat, saliva, body tissue, or any type of fluid under test. If required, the fluid under test can be diluted with water, added with a liquid or aqueous agent, or blended with an additive, etc. The signal transmission wiring 112 transmits a sensing signal Ss obtained according to the capacitance to the electronic circuit 13. The electronic circuit 13 is coupled to the signal transmission circuit 112 to receive and process the sensing signal Ss. For example, the sensing signal Ss can be used to detect a concentration of a specific component in the fluid, or used to obtain certain reading. The package layer 14 covers the electronic circuit 13 but does not cover the test region 111; the coverage of the package layer 14 outside the test region 111 is not limited to the way as shown in the figure but can be decided according to practical requirements. Thus, referring to FIG. 1B, an open platform 15 is defined by the test region 111, the metal spacer 12B, and the package layer 14, such that a user can easily put the fluid onto the test region with guidance of the spacers and the package layer, and no micro-channel is required.

As illustrated, the bio-detection device 10 of the present invention provides an open platform 15 for detection. The open platform 15 has benefits which do not exist in the prior bio-detection device. The benefits include: first, it is open and easy to put in the fluid under test. Second, the bio-detection device 10 does not need a large area for accommodating the main path and shunt paths, nor does it require a driving unit. In comparison with the prior art, the bio-detection device 10 and the open platform 15 of the present invention provide the benefits of easier detection control, simpler manufacturing process, easier quality control, and lower manufacturing cost.

Figure 2:
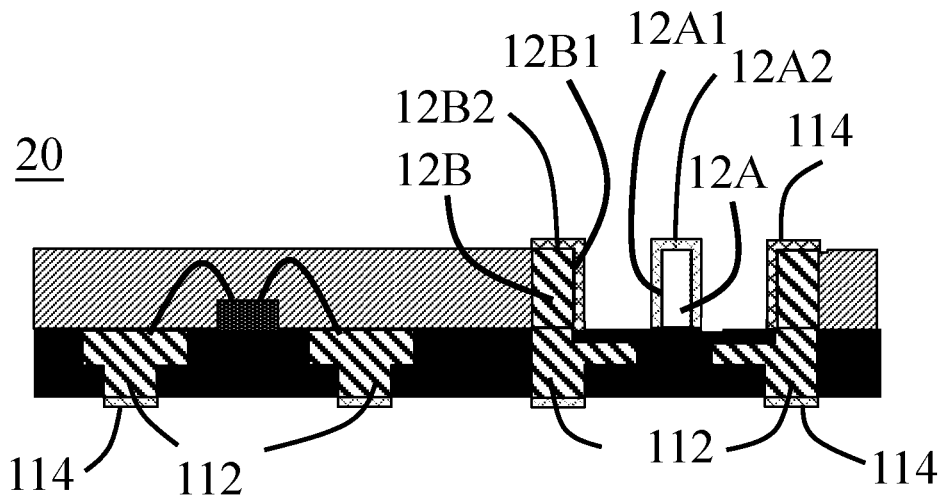
FIGS. 2-4 show bio-detection devices according to three embodiments of the present invention.
Figure 3:
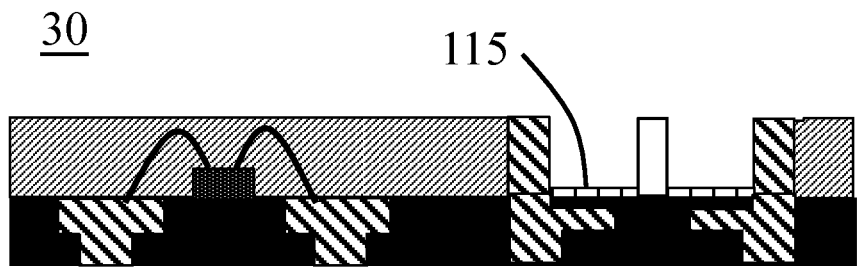
Figure 4:
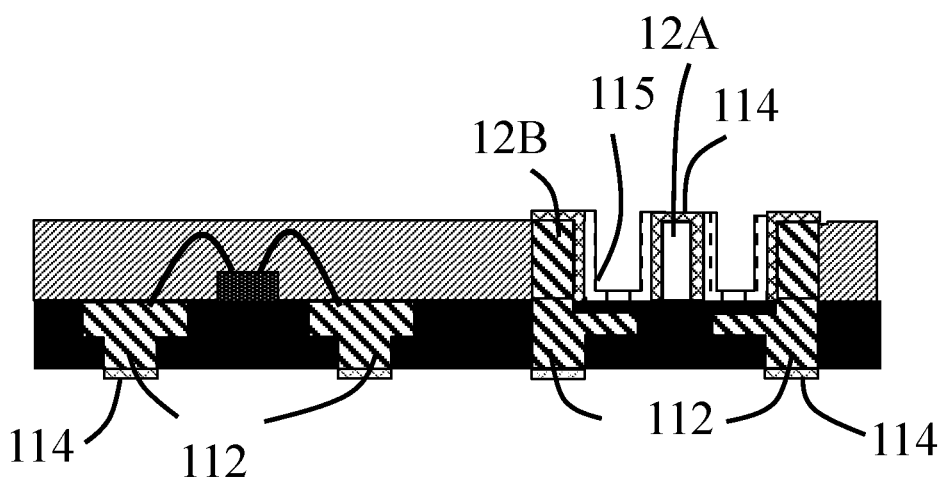

Please refer to FIGS. 2 and 3, the bio-detection device can be modified within the spirit of the present invention. For example, as shown in FIG. 2, the bio-detection device 20 can further include a rust-proof layer 114 on the exposed portions (i.e., exposed if without the rust-proof layer 114) of the metal spacers 12A and 12B which are located on the open platform. The rust-proof layer 114 for example can be, but is not limited to a gold-plating layer or other conductive anti-rust layer. FIG. 3 shows a bio-detection device 30 which is another embodiment, wherein the test region 111 is covered by a hydrophilic layer 115. The hydrophilic layer 115 covers a surface of the test region 111 which is to contact the fluid, and the hydrophilic layer 115 is located a portion of the open platform 15 where the rust-proof layer 114 does not cover. When the test region 111 receives and carries the fluid under test, the hydrophilic layer 115 helps to evenly distribute the fluid under test over the test region 111 by surface tension. FIG. 4 shows another embodiment which includes both the rust-proof layer 114 and the hydrophilic layer 115, wherein the hydrophilic layer 115 is located on the rust-proof layer 114 in the open platform 15 and located on a portion of the open platform 15 where the rust-proof layer 114 does not cover. The not-covered portion of the open platform 15 can be the test region 111, or smaller or larger than the test region 111.

Please refer to FIG. 2, wherein the rust-proof layer 114 can be manufactured by electroless plating on the sides 12A1 and 12B1, and tops 12A2 and 12B2 of the metal spacers 12A and 12B. Electroless plating itself is a well-known technique and its details are not redundantly described herein.

In one embodiment, the spacers 12A and 12B, and the signal transmission wiring 112 in the carrier 11, can be made of a conduction material or include a conduction material, such as a metal. For example, the material of the spacers 12A and 12B can include and is not limited to: copper, nickel, gold, palladium, copper alloy, nickel alloy, gold alloy, palladium alloy, or a combination thereof. Similarly, the material of the signal transmission wiring 112 in the carrier 11 can include and is not limited to: copper, nickel, gold, palladium, copper alloy, nickel alloy, gold alloy, palladium alloy, or a combination thereof.

In the embodiment shown in FIG. 1A, the electronic circuit 13 is located inside the carrier 11. However, in a different arrangement, the electronic circuit 13 can be located partially or completely outside the carrier 11, and is coupled to the carrier 11 by wiring (not shown). For example, for cost saving, signals from two or more carriers 11 can be received and processed by a single electronic circuit 13.

In one embodiment, the electronic circuit 13 can include a controller, an application-specific integrated circuit (ASIC), or other types of circuits, as required for processing the sensing signal.

In one embodiment, besides the signal transmission wiring 112 in the carrier 11 for transmitting sensing signal Ss between the electronic circuit 13 and the capacitor formed by the metal spacers 12A and 12B, there can be other signal transmission wirings (not shown) for transmitting signals within the electronic circuit 13 itself or for transmitting signals between the electronic circuit 13 and another electronic device. Because the metal spacers 12A and 12B are at different voltage levels, the signal transmission wiring 112 can include plural different signal lines respectively connected to the metal spacers 12A and 12B. That is, the term "signal transmission wiring" in the specification of the present invention is a collective term, which represents a set of plural signal lines.

Figure 5A:
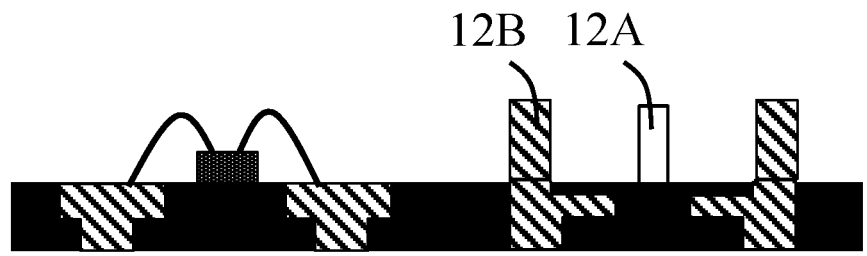
FIGS. 5A-5D show manufacturing steps of the package layer encapsulating the carrier according to one embodiment of the present invention.
Figure 5B:
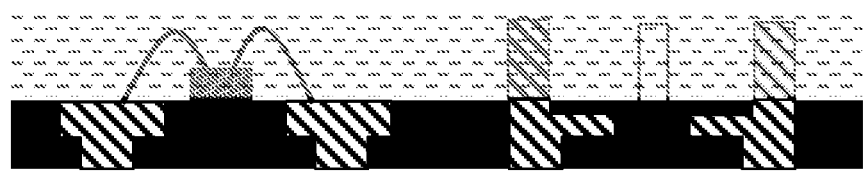
Figure 5C:
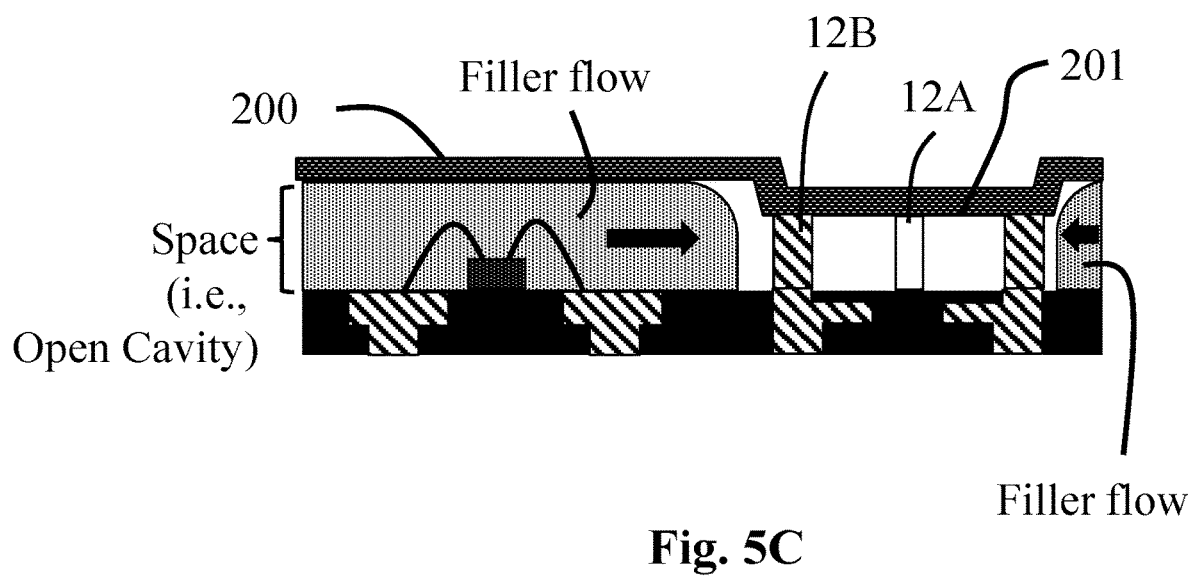
Figure 5D:
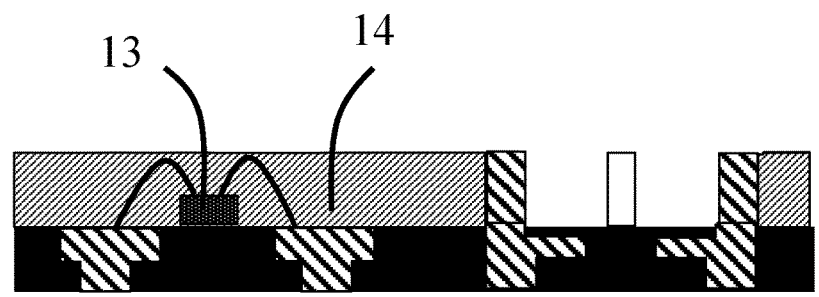

FIGS. 5A-5D show manufacturing steps of the package layer encapsulating the carrier according to one embodiment of the present invention. In this embodiment, an "open cavity molding" method is used to encapsulate the electronic circuit 13 and a portion of the carrier 11 which is outside the test region 111 and the metal spacers 12B. FIG. 5A shows a status of the carrier 11 which has not yet been encapsulated by the package layer, wherein the electronic circuit 13, the metal spacers 12A and 12B are located on the carrier 11. FIG. 5B shows that the carrier 11 which has not yet been encapsulated by the package layer can be subject to plasma cleaning and wetting to enhance surface cleanness and adhesion effect between the package layer material and metal. FIG. 5C shows that a space (i.e., open cavity) is formed between a molding plate 200 and the carrier 11 when the carrier 11 has not yet been encapsulated by the package layer. An extrusion 201 of the molding plate 200 is in contact with the outermost portion of metal spacer 12B (and the metal spacer 12A in this embodiment, but the contact with the metal spacer 12A is not necessary) for defining a limit to block a filler flow such that the filler flow does not pass beyond the metal spacer 12B to flow into the space between the extrusion 201 and the test region. The filler flow only flows below the molding plate 200, to the space outer than the outermost portion of metal spacer 12B. Please refer to FIG. 5D, wherein after the filler flow is solidified to form the package layer 14, the molding plate 200 is removed.

In this embodiment, the encapsulating range of the package layer 14 is defined by the extrusion 201 and the outermost portion of metal spacer 12B, so the package layer 14 is in contact with the outermost portion of metal spacer 12B. In another embodiment, the shape of the molding plate 200 can be modified to further include isolation walls for defining the encapsulating range of the package layer 14, and in this case the package layer 14 is not necessarily in contact with the outmost metal spacer 12B. For illustrative purpose, the carrier in this embodiment includes neither of the rust-proof layer nor the hydrophilic layer. However, if the rust-proof layer and hydrophilic layer are desired, the rust-proof layer and hydrophilic layer can be formed on the carrier 11 after the step of FIG. 5D. For example, the rust-proof layer and hydrophilic layer can be formed by electroless plating or coating steps.

As described in the above, the electronic circuit 13 can be completely, partially or not on the carrier 13. FIGS. 5A-5D show the manufacturing steps to form the package layer 14 encapsulating the carrier 11 with the electronic circuit 13 completely or partially on it. If the electronic circuit 13 is not on the carrier 11, the manufacturing steps of FIG. 5A to FIG. 5D still apply except that there is no electronic circuit 13 in these figures. By the open cavity molding method as described in the above, the package layer 14 encapsulates a portion of the carrier 11 outside the outermost metal spacer on the test region 111. According to the present invention, the package layer 14 can encapsulate the electronic circuit 13, or the package layer 14 does no encapsulate the electronic circuit 13.

Figure 6A:
FIGS. 6A-6H show manufacturing steps of the carrier according to one embodiment of the present invention.
Figure 6B:
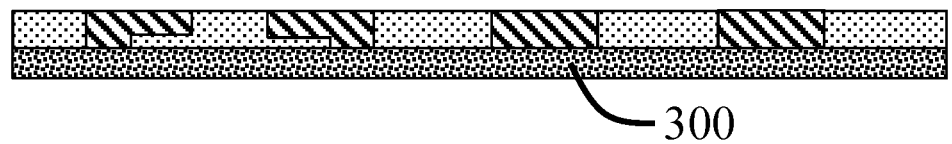
Figure 6C:
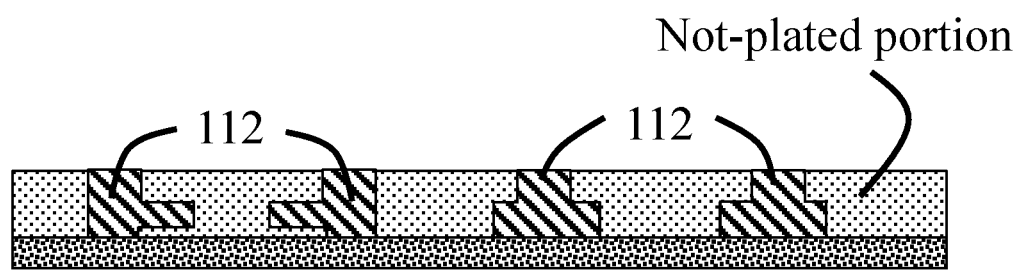
Figure 6D:
Figure 6E:
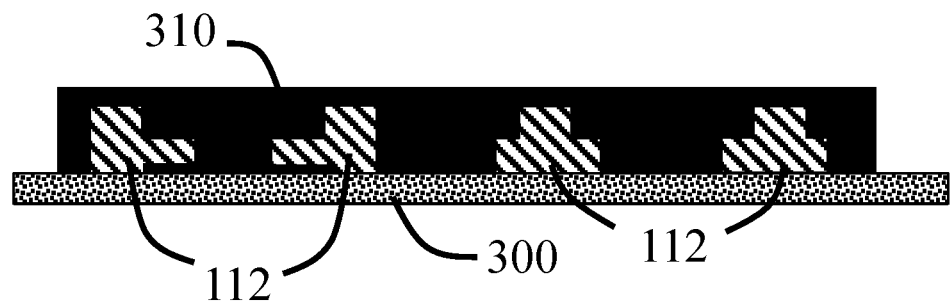
Figure 6F:
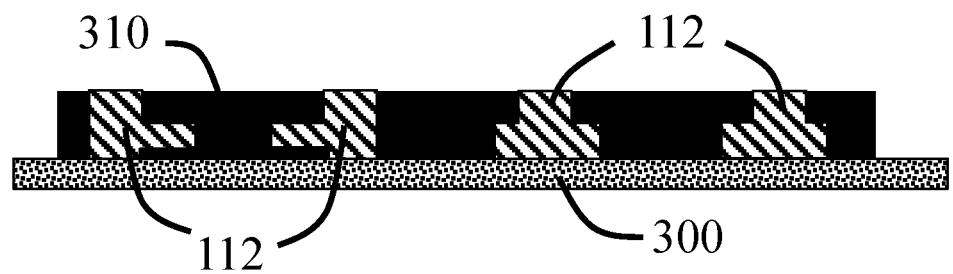
Figure 6G:
Figure 6H:
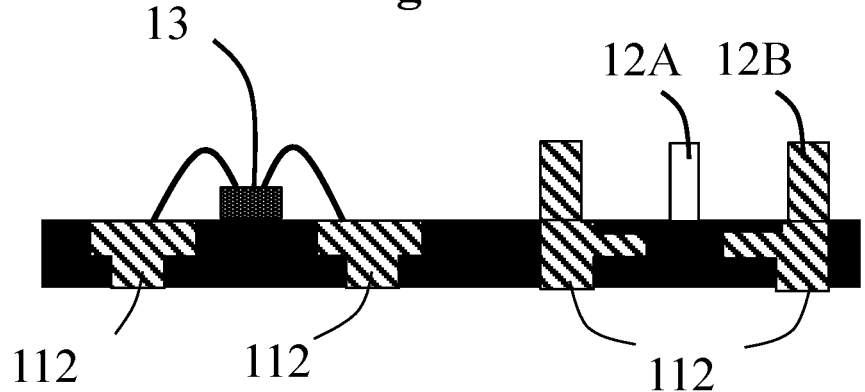

FIGS. 6A-6H show manufacturing steps of the carrier according to one embodiment of the present invention, wherein the carrier is manufactured by a "molded interconnect system" method. As shown in FIGS. 6A, 6B, and 6C, a substrate 300 is provided, and the signal transmission wiring 112 is formed on the substrate 300 by plating. FIG. 6A shows that a first layer of the signal transmission wiring 112 is formed on the substrate 300 by plating. FIG. 6B shows that a second layer of the signal transmission wiring 112 is formed by plating. If necessary, more layers of the signal transmission wiring 112 can be formed on the substrate 300, and FIG. 6C shows one embodiment of the multi-layer structure. The steps and structure shown in FIGS. 6A, 6B, and 6C are just one illustrative example; the layers and layout of the signal transmission wiring 112 can be modified according to practical requirements. FIG. 6D shows that the not-plated portions on the substrate 300 (referring to FIG. 6C) are removed. In FIG. 6E, the substrate 300 and the signal transmission wiring 112 on the substrate 300 are encapsulated by a filler layer 310. In FIG. 6F, the height of the filler layer 310 is reduced in order to expose the signal transmission wiring 112 on a surface of the filler layer 310. This height-reduction step is for transmitting signals through a bottom side of the carrier 11 (referring to FIGS. 1A, 1B, and 2-4); however, if the signal transmission through the bottom side of the carrier 11 is not needed, the height-reduction step can be omitted. The height reduction of the filler layer 310 can be done for example by grinding or etching the filler layer 310. In FIG. 6G, the substrate 300 is removed from the filler layer 310 such that the signal transmission wiring 112 is exposed on another surface of the filler layer 310, wherein this "another surface" is the top surface of the carrier 11 as shown in FIGS. 1A, 1B, 2, and 4. The carrier 11 in FIG. 6H is flipped up-side-down as compared with FIG. 6G, wherein the metal spacers 12A and 12B are formed on the signal transmission wiring 112, and the electronic circuit 13 is mounted on the carrier to electrically connect the signal transmission wiring 112. If the electronic circuit 13 is not located on the carrier 11, the step of mounting the electronic circuit 13 on the carrier 11 can be omitted.

The material of the aforementioned filler layer can be the same as or different from the material of the package layer. In one embodiment, for better adhesion effect, the material of the filler layer can be the same as the material of the package layer. In another embodiment, to prevent the filler flow of the package layer from affecting the size and the structure of the filler layer, the material of the filler layer material preferably has a higher melting point than the melting point of the material of the package layer, such that the step of forming the package layer does not cause any deformation of the filler layer. In this case, the materials of the filler layer and the package layer are different. The materials of the filler layer and the package layer can be decided according to practical requirements.

Figure 7A:
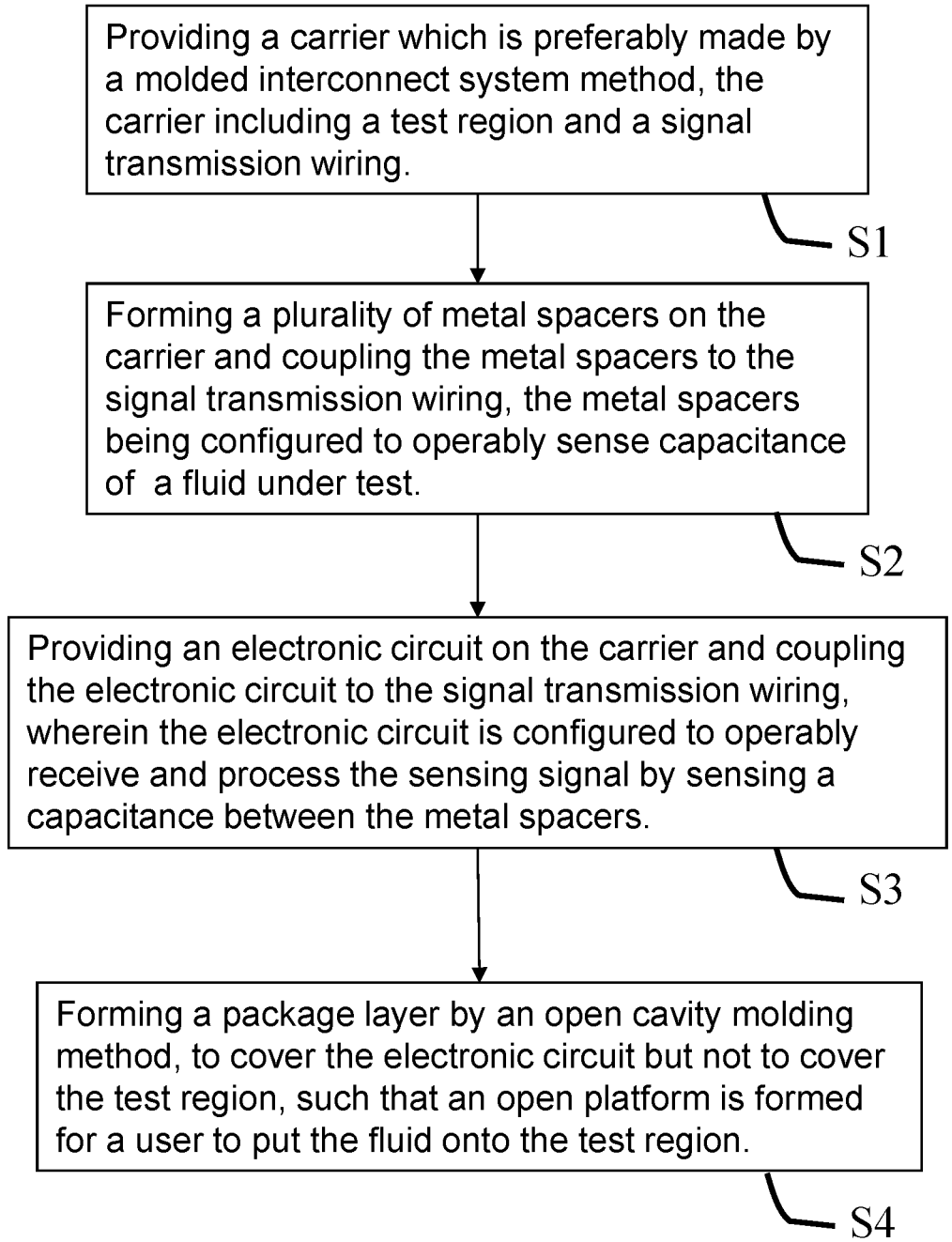
FIG. 7A shows manufacturing steps of the bio-detection device according to one embodiment of the present invention.

Please refer to FIG. 7A, in one perspective, the present invention provides a manufacturing method of a bio-detection device. The manufacturing method includes: providing a carrier, which is preferably made by a molded interconnect system method as shown in FIGS. 6A-6G, the carrier including a test region and a signal transmission wiring (S1); forming a plurality of metal spacers on the carrier and coupling the metal spacers to the signal transmission wiring, the metal spacers being configured to operably sense capacitance of a fluid under test (S2); providing an electronic circuit on the carrier and coupling the electronic circuit to the signal transmission wiring, wherein the electronic circuit is configured to operably receive and process the sensing signal by sensing a capacitance between the metal spacers; for example, the electronic circuit can be used to calculate a component concentration of the fluid according to the sensing signal (S3); and forming a package layer by an open cavity molding method, to cover the electronic circuit but not to cover the test region, such that an open platform is formed for the user to put the fluid onto the test region (S4).

Figure 7B:
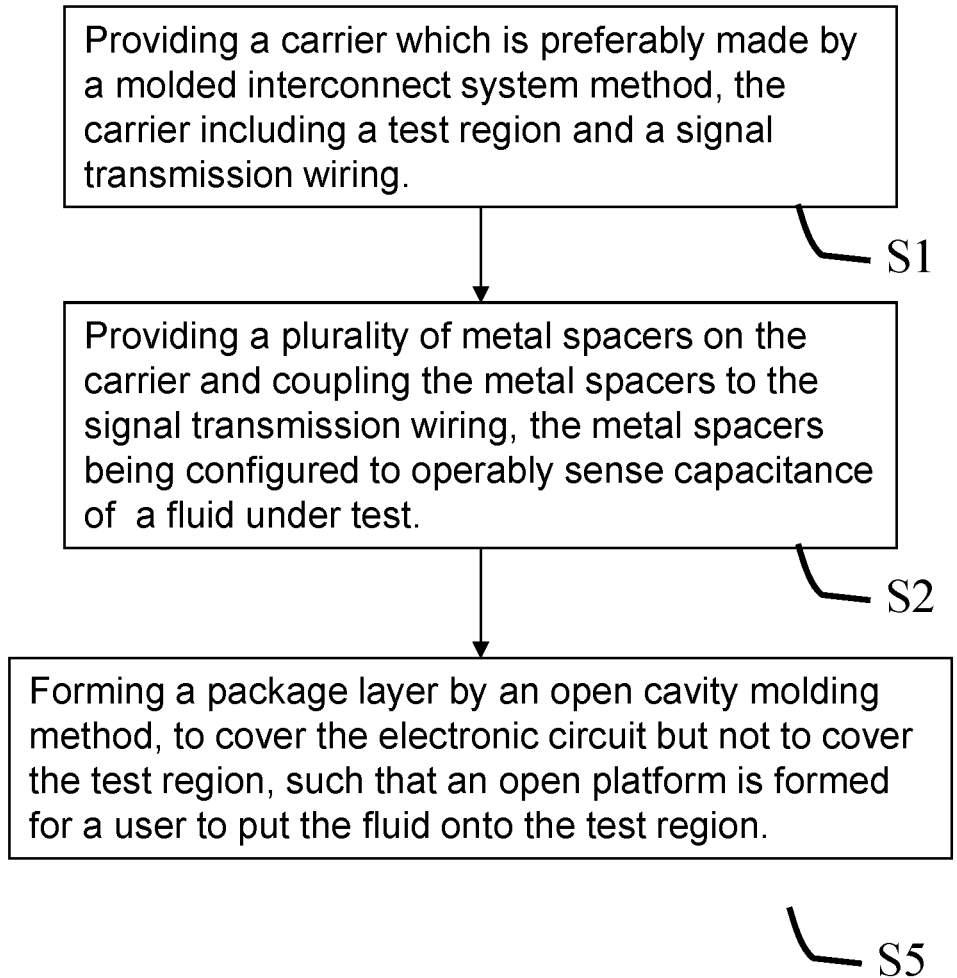
FIG. 7B shows manufacturing steps of the bio-detection device according to another embodiment of the present invention.

Please refer to FIG. 7B, wherein if the electronic circuit is not located on the carrier, the manufacturing method after step S2 can go direct to step S5. The step S5 includes: forming a package layer by an open cavity molding method, to cover a portion of the carrier nut not to cover the test region, such that an open platform is formed for the user to put the fluid onto the test region.

The present invention has been described in considerable detail with reference to certain preferred embodiments thereof. It should be understood that the description is for illustrative purpose, not for limiting the scope of the present invention. Those skilled in this art can readily conceive variations and modifications within the spirit of the present invention; for example, there may be additional devices or circuits inserted between two devices or circuits shown to be in direct connection in the embodiments, as long as such inserted devices or circuits (such as a switch, a diode, a resistor, a filter, etc.) do not affect the primary function of the circuitry. Besides, an embodiment or a claim of the present invention does not need to attain or include all the objectives, advantages or features described in the above. The abstract and the title are provided for assisting searches and not to be read as limitations to the scope of the present invention. It is not limited for each of the embodiments described hereinbefore to be used alone; under the spirit of the present invention, two or more of the embodiments described hereinbefore can be used in combination. For example, two or more of the embodiments can be used together, or, a part of one embodiment can be used to replace a corresponding part of another embodiment.

What is claimed is:

1. A manufacturing method of a bio-detection device, comprising:

provide a carrier, which includes a test region and a signal transmission wiring;

forming a plurality of spacers on the carrier and coupling the spacers to the signal transmission wiring, the spacers being configured to operably sense a capacitance of a fluid under test; and forming a package layer by a process of open cavity molding, to cover a portion of the carrier but not to cover the test region, whereby an open platform is defined for the fluid under test to be put in.

2. The manufacturing method of a bio-detection device of claim 1, further comprising: forming an electronic circuit on the carrier and coupling the electronic circuit to the signal transmission wiring, wherein the electronic circuit is configured to operably receive and process a sensing signal generated by the spacers.

3. The manufacturing method of a bio-detection device of claim 2, wherein the package layer encapsulates the electronic circuit.

4. The manufacturing method of a bio-detection device of claim 1, wherein the carrier is manufactured by steps including:

providing a substrate;

forming the signal transmission wiring on the substrate;

encapsulating both the substrate and the signal transmission wiring on the substrate by a filler layer; and removing the substrate to expose a portion of the signal transmission wiring on a first surface of the filler layer.

5. The manufacturing method of a bio-detection device of claim 4, wherein the manufacturing steps of the carrier further include: grinding the filler layer such that another portion of the signal transmission circuit is exposed on a second surface of the filler layer, wherein the second surface is opposite to the first surface.

6. The manufacturing method of a bio-detection device of claim 1, wherein the process of open cavity molding for forming the package layer includes:

providing a molding plate in contact with the carrier or at least one of the spacers on the carrier;

filling a filler flow on the carrier, wherein the spacers form a structure which blocks the filler flow from flowing onto the test region;

solidifying the filler flow to form the package layer; and removing the molding plate.

7. The manufacturing method of a bio-detection device of claim 6, wherein the molding plate includes an extrusion, and when the molding plate is in contact with at least one of the spacers, the extrusion is in contact with an outermost one of the spacers, to block the filler flow from flowing onto the test region.

* * * * *